(12) United States Patent
Begtrup et al.

(10) Patent No.: US 10,674,946 B2
(45) Date of Patent: Jun. 9, 2020

(54) SWEAT SENSING DEVICES WITH SENSOR ABRASION PROTECTION

(71) Applicant: Eccrine Systems, Inc., Cincinnati, OH (US)

(72) Inventors: Gavi Begtrup, Cincinnati, OH (US); Jason Heikenfeld, Cincinnati, OH (US)

(73) Assignee: Eccrine Systems, Inc., Cincinnati, OH (US)

( * ) Notice: Subject to any disclaimer, the term of this patent is extended or adjusted under 35 U.S.C. 154(b) by 518 days.

(21) Appl. No.: 15/382,703

(22) Filed: Dec. 18, 2016

(65) Prior Publication Data

US 2017/0172470 A1   Jun. 22, 2017

Related U.S. Application Data

(60) Provisional application No. 62/269,254, filed on Dec. 18, 2015.

(51) Int. Cl.
 *A61B 5/145* (2006.01)
 *A61N 1/04* (2006.01)
 *A61B 5/00* (2006.01)

(52) U.S. Cl.
 CPC ........ *A61B 5/14521* (2013.01); *A61B 5/4266* (2013.01); *A61N 1/0428* (2013.01); *A61B 2562/18* (2013.01)

(58) Field of Classification Search
 CPC .............. A61B 5/14521; A61B 5/4266; A61B 2562/18; A61B 5/6819; A61B 5/0059; A61B 5/02427; A61B 5/14552; A61B 5/6838; A61B 5/7405; A61B 5/742; A61B 5/746; A61B 5/0022; A61B 5/01;
 (Continued)

(56) References Cited

U.S. PATENT DOCUMENTS 4,190,060 A    2/1980  Greenleaf et al.
4,457,748 A *  7/1984  Lattin .................. A61N 1/0428
                                              600/573
(Continued)

FOREIGN PATENT DOCUMENTS

EP    0282349 A2   9/1988
EP    0453283 A1   10/1991
(Continued)

OTHER PUBLICATIONS

Prausnitz et al., "Transdermal Drug Delivery", Nat Biotechnol, 26(11), pp. 1261-1268, 2008.*
(Continued)

*Primary Examiner* — Eric F Winakur
(74) *Attorney, Agent, or Firm* — Chad G. Clark

(57) ABSTRACT

The disclosed invention provides a sweat sensing device configured with self-aligned sweat stimulation means to provide adequate sweat generation for continuous monitoring of sweat. The disclosed device includes one or more analyte-specific sweat sensors that self-align with sweat glands. In one embodiment, the sweat sensing device includes means to protect the self-aligning sensors from abrasion against the skin or device components. In another embodiment, the device includes prolonged sweat stimulation for the self-aligning sensors through diffusion of a sweat stimulating compound into the skin.

16 Claims, 8 Drawing Sheets

(58) Field of Classification Search
CPC ... A61B 5/087; A61B 5/14532; A61B 5/6825; A61B 5/6833; A61B 2560/0223; A61B 2562/0204; A61B 2562/04; A61N 1/0428

See application file for complete search history.

(56) References Cited

U.S. PATENT DOCUMENTS

| | | |
|---|---|---|
| 4,542,751 A | 9/1985 | Webster et al. |
| 4,756,314 A | 7/1988 | Eckenhoff et al. |
| 4,820,263 A | 4/1989 | Spevak et al. |
| 4,846,182 A * | 7/1989 | Fogt ............ A61B 5/4266 600/362 |
| 5,036,861 A | 8/1991 | Sembrowich et al. |
| 5,050,604 A | 9/1991 | Reshef et al. |
| 5,140,985 A | 8/1992 | Schroeder et al. |
| 5,246,003 A | 9/1993 | Delonzor |
| 5,437,999 A | 8/1995 | Diebold et al. |
| 5,438,984 A | 8/1995 | Schoendorfer |
| 5,556,789 A | 9/1996 | Goerlach-Graw et al. |
| 5,690,893 A | 11/1997 | Ozawa et al. |
| 5,814,599 A | 9/1998 | Mitragotri et al. |
| 5,944,662 A | 8/1999 | Schoendorfer |
| 6,175,752 B1 | 1/2001 | Say et al. |
| 6,198,953 B1 | 3/2001 | Webster et al. |
| 6,256,533 B1 | 7/2001 | Yuzhakov et al. |
| 6,269,265 B1 | 7/2001 | Anderson |
| 6,299,578 B1 | 10/2001 | Kurnik et al. |
| 6,592,529 B2 | 7/2003 | Marett |
| 6,666,821 B2 | 12/2003 | Keimel |
| 7,044,911 B2 | 5/2006 | Drinan et al. |
| 7,190,986 B1 | 3/2007 | Hannula et al. |
| 7,219,534 B2 | 5/2007 | Campbell |
| 7,378,054 B2 | 5/2008 | Karmali |
| 7,383,072 B2 | 6/2008 | Edmonson et al. |
| 7,384,396 B2 | 6/2008 | Samuels et al. |
| 7,749,445 B2 | 7/2010 | Masters |
| 7,800,494 B2 | 9/2010 | Kim |
| 7,813,780 B2 | 10/2010 | Shah et al. |
| 7,842,234 B2 | 11/2010 | Lauks et al. |
| 7,959,791 B2 | 6/2011 | Kjaer et al. |
| 8,125,539 B2 | 2/2012 | Takashima |
| 8,128,889 B2 | 3/2012 | Fujimoto et al. |
| 8,252,248 B2 | 8/2012 | Kramer |
| 8,391,946 B2 | 3/2013 | Sugenoya et al. |
| 8,565,850 B2 | 10/2013 | Martinsen et al. |
| 8,593,287 B2 | 11/2013 | Hayter et al. |
| 8,617,067 B2 | 12/2013 | Jain et al. |
| 9,133,024 B2 | 9/2015 | Phan et al. |
| 9,867,539 B2 | 1/2018 | Heikenfeld et al. |
| 2002/0091312 A1 | 7/2002 | Berner et al. |
| 2003/0135100 A1 | 7/2003 | Kim et al. |
| 2003/0201194 A1 | 10/2003 | Heller et al. |
| 2004/0215098 A1 | 10/2004 | Barton et al. |
| 2004/0249310 A1 | 12/2004 | Shartle et al. |
| 2004/0260154 A1 | 12/2004 | Sidelnik et al. |
| 2004/0267189 A1 | 12/2004 | Mavor et al. |
| 2005/0069925 A1 | 3/2005 | Ford et al. |
| 2005/0106713 A1 | 5/2005 | Phan et al. |
| 2005/0177035 A1 | 8/2005 | Botvinick et al. |
| 2005/0192528 A1 | 9/2005 | Tapper |
| 2005/0197554 A1 | 9/2005 | Polcha |
| 2005/0228297 A1 | 10/2005 | Banet et al. |
| 2005/0280531 A1 | 12/2005 | Fadem et al. |
| 2006/0009697 A1 | 1/2006 | Banet et al. |
| 2006/0062852 A1 | 3/2006 | Holmes |
| 2006/0127964 A1 | 6/2006 | Ford et al. |
| 2006/0253011 A1 | 11/2006 | Edmonson et al. |
| 2006/0254341 A1 | 11/2006 | Campbell |
| 2007/0027383 A1 | 2/2007 | Peyser et al. |
| 2007/0032731 A1 | 2/2007 | Lovejoy et al. |
| 2007/0179371 A1 | 8/2007 | Peyser et al. |
| 2008/0015494 A1 | 1/2008 | Santini, Jr. et al. |
| 2008/0045816 A1 | 2/2008 | Jang et al. |
| 2008/0154179 A1 | 6/2008 | Cantor et al. |
| 2008/0286349 A1 | 11/2008 | Nomoto et al. |
| 2008/0306362 A1 | 12/2008 | Davis |
| 2009/0076345 A1 | 3/2009 | Manicka et al. |
| 2009/0159442 A1 | 6/2009 | Collier et al. |
| 2009/0204008 A1 | 8/2009 | Beilin |
| 2009/0270704 A1 | 10/2009 | Peyser et al. |
| 2010/0044224 A1 | 2/2010 | Kataky |
| 2010/0063372 A1 | 3/2010 | Potts et al. |
| 2010/0130843 A1 | 5/2010 | Caceres Galvez et al. |
| 2010/0132485 A1 | 6/2010 | Erez et al. |
| 2010/0198521 A1 | 8/2010 | Haick |
| 2011/0004072 A1 | 1/2011 | Fletcher et al. |
| 2011/0054273 A1 | 3/2011 | Omoda |
| 2011/0079521 A1 | 4/2011 | Revol-Cavalier |
| 2011/0118656 A1 | 5/2011 | Eckhoff et al. |
| 2011/0178380 A1 | 7/2011 | Chowdhury |
| 2011/0196283 A1 | 8/2011 | Imran et al. |
| 2011/0208458 A1 | 8/2011 | Pinter et al. |
| 2011/0275918 A1 | 11/2011 | Yamashita et al. |
| 2012/0004570 A1 | 1/2012 | Shimizu et al. |
| 2012/0028283 A1 | 2/2012 | Hoss et al. |
| 2012/0119906 A1 | 5/2012 | Kountotsis |
| 2012/0123220 A1 | 5/2012 | Iyer et al. |
| 2012/0150072 A1* | 6/2012 | Revol-Cavalier ............ A61B 5/14517 600/573 |
| 2012/0165626 A1 | 6/2012 | Irina et al. |
| 2012/0191147 A1 | 7/2012 | Rao et al. |
| 2012/0209226 A1 | 8/2012 | Simmons et al. |
| 2012/0229661 A1 | 9/2012 | Sekiguchi et al. |
| 2012/0244097 A1* | 9/2012 | Lu ............ A01N 25/00 424/64 |
| 2012/0277697 A1 | 11/2012 | Haghgooie et al. |
| 2012/0285829 A1 | 11/2012 | Mount et al. |
| 2012/0317430 A1 | 12/2012 | Rahman et al. |
| 2013/0006079 A1 | 1/2013 | Feldman et al. |
| 2013/0010108 A1 | 1/2013 | Hashizume et al. |
| 2013/0013028 A1 | 1/2013 | Kriksunov et al. |
| 2013/0053668 A1 | 2/2013 | Lin |
| 2013/0079605 A1 | 3/2013 | Bandaru et al. |
| 2013/0099937 A1 | 4/2013 | Azimi |
| 2013/0108667 A1 | 5/2013 | Soikum et al. |
| 2013/0123595 A1 | 5/2013 | Currie et al. |
| 2013/0183399 A1 | 7/2013 | Blow et al. |
| 2013/0245388 A1 | 9/2013 | Rafferty et al. |
| 2013/0306491 A1 | 11/2013 | Briman et al. |
| 2013/0317318 A1 | 11/2013 | Tartz et al. |
| 2013/0317333 A1 | 11/2013 | Yang et al. |
| 2014/0012114 A1 | 1/2014 | Zevenbergen et al. |
| 2014/0025000 A1 | 1/2014 | Currie et al. |
| 2014/0206977 A1 | 7/2014 | Bahney et al. |
| 2014/0221792 A1 | 8/2014 | Miller et al. |
| 2014/0275862 A1 | 9/2014 | Kennedy |
| 2014/0276220 A1 | 9/2014 | Briscoe et al. |
| 2014/0343371 A1 | 11/2014 | Sowers, II et al. |
| 2015/0057515 A1 | 2/2015 | Hagen et al. |
| 2015/0112164 A1 | 4/2015 | Heikenfeld et al. |
| 2015/0112165 A1 | 4/2015 | Heikenfeld |
| 2015/0289820 A1 | 4/2015 | Miller et al. |
| 2016/0058354 A1 | 3/2016 | Phan et al. |
| 2016/0066828 A1 | 3/2016 | Phan et al. |
| 2016/0157768 A1 | 6/2016 | Braig et al. |
| 2017/0100035 A1 | 4/2017 | Heikenfeld |
| 2017/0100071 A1 | 4/2017 | Heikenfeld |
| 2017/0215773 A1 | 8/2017 | Heikenfeld et al. |

FOREIGN PATENT DOCUMENTS

| | | |
|---|---|---|
| EP | 1575010 A1 | 9/2005 |
| EP | 1637889 A1 | 3/2006 |
| EP | 2551784 A1 | 1/2013 |
| EP | 2783725 A1 | 10/2014 |
| WO | 1990011519 A1 | 10/1990 |
| WO | 1994014062 A1 | 6/1994 |
| WO | 2000014535 A1 | 3/2000 |
| WO | 2001088525 A1 | 11/2001 |
| WO | 2006133101 A2 | 12/2006 |
| WO | 2007097754 A1 | 8/2007 |
| WO | 2007146047 A1 | 12/2007 |
| WO | 2008058014 A2 | 5/2008 |

(56) References Cited

FOREIGN PATENT DOCUMENTS

| | | |
|---|---|---|
| WO | 2008083687 A1 | 7/2008 |
| WO | 2008095940 A1 | 8/2008 |
| WO | 2009004001 A1 | 1/2009 |
| WO | 2009052321 A2 | 4/2009 |
| WO | 2010017578 A1 | 2/2010 |
| WO | 2011008581 A2 | 1/2011 |
| WO | 2011117952 A1 | 9/2011 |
| WO | 2013111409 A1 | 8/2013 |
| WO | 2013181436 A1 | 12/2013 |
| WO | 2014001577 A1 | 1/2014 |
| WO | 2014025430 A3 | 5/2014 |
| WO | 2015058065 A1 | 4/2015 |
| WO | 2016007944 A2 | 1/2016 |
| WO | 2016049019 A1 | 3/2016 |
| WO | 2016090189 A1 | 6/2016 |
| WO | 2016130905 A1 | 8/2016 |
| WO | 2016138087 A1 | 9/2016 |
| WO | 2017019602 A1 | 2/2017 |
| WO | 2017070640 A1 | 4/2017 |

OTHER PUBLICATIONS

Banga, "Electrically Assisted Transdermal and Topical Drug Delivery", CRC Press, pp. 64, 2002.*
International Searching Authority, Search Report issued in corresponding International Application No. PCT/US2016/43771 dated Dec. 8, 2016, 4 pages.
International Searching Authority, Written Opinion issued in corresponding International Application No. PCT/US2016/43771 dated Dec. 8, 2016, 9 pages.
International Searching Authority, Search Report and Written Opinion issued in corresponding International Application No. PCT/US2016/58356 dated Jan. 6, 2017, 15 pages.
International Searching Authority, Search Report and Written Opinion issued in corresponding International Application No. PCT/US2016/58357 dated Jan. 19, 2017, 9 pages.
International Searching Authority, Search Report and Written Opinion issued in corresponding International Application No. PCT/US2017/047808 dated Nov. 6, 2017, 10 pages.

* cited by examiner

SWEAT SENSING DEVICES WITH SENSOR ABRASION PROTECTION

STATEMENT REGARDING FEDERALLY SPONSORED RESEARCH OR DEVELOPMENT

No federal funds were utilized for this invention.

CROSS-REFERENCE TO RELATED APPLICATIONS

This application relates to U.S. Provisional Application No. 62/269,254, filed Dec. 18, 2015, and has specification that relates to PCT/US2016/043771, the disclosures of which are hereby incorporated by reference herein in their entirety.

BACKGROUND OF THE INVENTION

Sweat sensing technologies have enormous potential for applications ranging from athletics, to neonatology, to pharmacological monitoring, to personal digital health, to name a few applications. Sweat contains many of the same biomarkers, chemicals, or solutes that are carried in blood and can provide significant information enabling one to diagnose illness, health status, exposure to toxins, performance, and other physiological attributes even in advance of any physical sign. Furthermore, sweat itself, the action of sweating, and other parameters, attributes, solutes, or features on, near, or beneath the skin can be measured to further reveal physiological information.

If sweat has such significant potential as a sensing paradigm, then why has it not emerged beyond decades-old usage in infant chloride assays for Cystic Fibrosis or in illicit drug monitoring patches? In decades of sweat sensing literature, the majority of practitioners in the art use the crude, slow, and inconvenient process of sweat stimulation, collection of a sample, transport of the sample to a lab, and then analysis of the sample by a bench-top machine and a trained expert. This process is so labor intensive, complicated, and costly that in most cases, one would just as well implement a blood draw since it is the gold standard for most forms of high performance biomarker sensing. Hence, sweat sensing has not emerged into its fullest opportunity and capability for biosensing, especially for continuous or repeated biosensing or monitoring. Furthermore, attempts at using sweat to sense "holy grails" such as glucose have not yet produced viable commercial products, reducing the publically perceived capability and opportunity space for sweat sensing.

Of all the other physiological fluids used for bio monitoring (e.g., blood, urine, saliva, tears), sweat has arguably the least predictable sampling rate in the absence of technology. However, with proper application of technology, sweat can be made to outperform other non-invasive or less invasive biofluids in predictable sampling.

For example, it is difficult to control saliva or tear rate without negative consequences for the user (e.g., dry eyes, tears, dry mouth, or excessive saliva while talking). Urine is also a difficult fluid for physiological monitoring, because it is inconvenient to take multiple urine samples, it is not always possible to take a urine sample when needed, and control of biomarker dilution in urine imposes further significant inconveniences on the user or test subject.

Known and existing methods of reducing sweat volume and increasing sampling rate predictability include those reported frequently in the clinical literature, such as coating the skin with petroleum jelly or oil through which sweat can push. However, these techniques have been demonstrated only for sweat collection and are not necessarily compatible with a wearable sensor. For example, petroleum jelly would wet against the sensor and effectively seal it from any sweat. Furthermore, other possible sweat pressure-activated methods must somehow be affixed to skin so that sweat is confined horizontally (otherwise sweat pressure activation is not possible). Conventional approaches will not work with wearable sensors, and inventive steps are required for enablement. Clearly, the state of art is lacking in devices to properly reduce the volume between sensors and skin, which is critical for fast sampling times or for sampling during intervals with very low sweat rates. In addition, it also may be critical for prolonged stimulation (i.e., where less stimulation is required over longer periods), and for improving biomarker measurements where a low sweat rate is required to ensure correlation between biomarker concentrations in sweat and those in blood.

One novel method of reducing sweat volume as disclosed in PCT/US2016/043771 involves using pressure-activated sealants to horizontally confine sweat flow and reduce sweat volume. In order to reduce sweat volume, however, sweat pressure-activated methods also require the sensor to be properly aligned with sweat glands, which can prove difficult. Since it would be impractical for sweat sensing device users to reliably place a device in ideal alignment with sweat glands, devices may be designed to optimize sweat gland coverage when the device is randomly placed on skin. However, even with such designs, sweat gland density may vary with between individuals, or even body location on the same individual. Therefore, a sweat sensing device that is self-aligning with sweat glands may improve sensor proximity to sweat glands under a variety of circumstances, thereby reducing sweat volume.

However, self-aligning sweat sensing designs must also be configured to access prolonged sweat stimulation, which is a significant challenge. Further, as with other referenced means of reducing sweat volume, self-aligning sensors must also be protected from abrasion. The disclosed invention, therefore, discloses a means of providing prolonged sweat stimulation for abrasion-protected self-aligning sensors by configuring a sweat-stimulating chemical in close proximity to the sensors, and enabling sudomotor axon reflex sweat response through diffusion of the sweat stimulation compound into the skin.

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sweat sensing technology into intimate proximity with sweat as it is generated. With such an invention, sweat sensing could become a compelling new paradigm as a biosensing platform.

SUMMARY OF THE INVENTION

The disclosed invention provides a sweat sensing device configured with self-aligned sweat stimulation means to provide adequate sweat generation for continuous monitoring of sweat. The disclosed device includes one or more analyte-specific sweat sensors that self-align with sweat glands. In one embodiment, the sweat sensing device includes means to protect the self-aligning sensors from abrasion against the skin or device components. In another embodiment, the device includes prolonged sweat stimulation for the self-aligning sensors through diffusion of a sweat stimulating compound into the skin.

BRIEF DESCRIPTION OF THE DRAWINGS

The objects and advantages of the disclosed invention will be further appreciated in light of the following detailed descriptions and drawings in which.

DEFINITIONS

Figure 1:
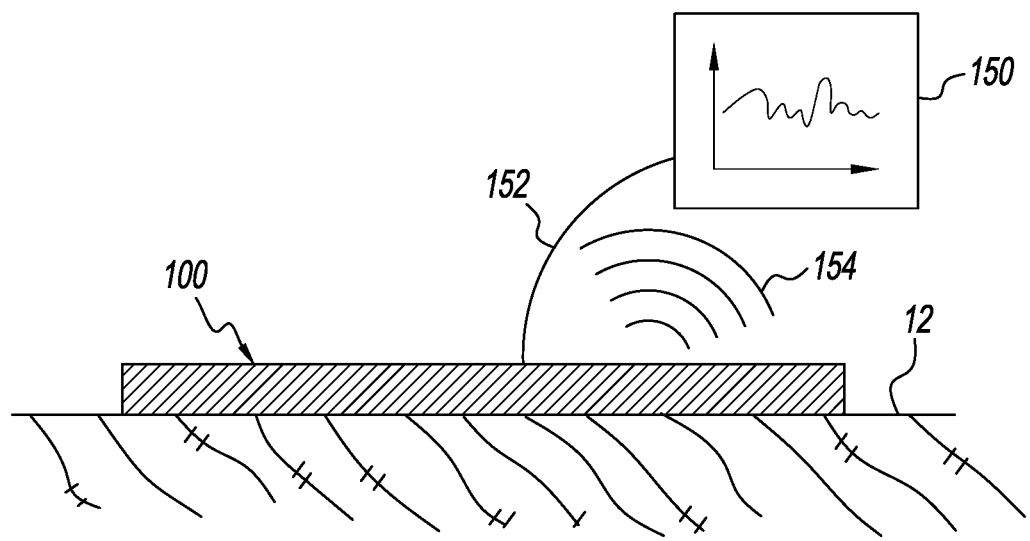
FIG. 1 depicts at least a portion of a wearable device for sweat biosensing.

As used herein, "sweat" means a biofluid that is primarily sweat, such as eccrine or apocrine sweat, and may also include mixtures of biofluids such as sweat and blood, or sweat and interstitial fluid, so long as advective transport of the biofluid mixtures (e.g., flow) is primarily driven by sweat.

"Continuous monitoring" means the capability of a device to provide at least one measurement of sweat determined by a continuous or multiple collection and sensing of that measurement or to provide a plurality of measurements of sweat over time.

"Chronological assurance" means the sampling rate or sampling interval that assures measurement(s) of analytes in sweat in terms of the rate at which measurements can be made of new sweat analytes emerging from the body. Chronological assurance may also include a determination of the effect of sensor function, potential contamination with previously generated analytes, other fluids, or other measurement contamination sources for the measurement(s). Chronological assurance may have an offset for time delays in the body (e.g., a well-known 5 to 30 minute lag time between analytes in blood emerging in interstitial fluid), but the resulting sampling interval (defined below) is independent of lag time, and furthermore, this lag time is inside the body, and therefore, for chronological assurance as defined above and interpreted herein, this lag time does not apply.

As used herein, "determined" may encompass more specific meanings including but not limited to: something that is predetermined before use of a device; something that is determined during use of a device; something that could be a combination of determinations made before and during use of a device.

As used herein, "sweat sampling rate" is the effective rate at which new sweat, or sweat solutes, originating from the sweat gland or from skin or tissue, reaches a sensor that measures a property of sweat or its solutes. Sweat sampling rate, in some cases, can be far more complex than just sweat generation rate. Sweat sampling rate directly determines, or is a contributing factor in determining the chronological assurance. Times and rates are inversely proportional (rates having at least partial units of 1/seconds), therefore a short or small time required to refill a sweat volume can also be said to have a fast or high sweat sampling rate. The inverse of sweat sampling rate (1/s) could also be interpreted as a "sweat sampling interval(s)". Sweat sampling rates or intervals are not necessarily regular, discrete, periodic, discontinuous, or subject to other limitations. Like chronological assurance, sweat sampling rate may also include a determination of the effect of potential contamination with previously generated sweat, previously generated solutes, other fluid, or other measurement contamination sources for the measurement(s). Sweat sampling rate can also be in whole or in part determined from solute generation, transport, advective transport of fluid, diffusion transport of solutes, or other factors that will impact the rate at which new sweat or sweat solutes reach a sensor and/or are altered by older sweat or solutes or other contamination sources. Sensor response times may also affect sampling rate.

As used herein, "sweat stimulation" is the direct or indirect causing of sweat generation by any external stimulus, the external stimulus being applied for the purpose of stimulating sweat. One example of sweat stimulation is the administration of a sweat stimulant such as pilocarpine. Going for a jog, which stimulates sweat, is only sweat stimulation if the subject jogging is jogging for the purpose of stimulating sweat.

Sudomotor axon reflex (SAR) is a biological response in which innervation of sweat glands occurs as a result of peripheral functionality of sudomotor units (i.e., the body will stimulate a group of sweat glands near the direct stimulation region).

As used herein, "sweat generation rate" is the rate at which sweat is generated by the sweat glands themselves. Sweat generation rate is typically measured by the flow rate from each gland in nL/min/gland. In some cases, the measurement is then multiplied by the number of sweat glands from which the sweat is being sampled.

As used herein, "measured" can imply an exact or precise quantitative measurement and can include broader meanings such as, for example, measuring a relative amount of change of something. Measured can also imply a binary measurement, such as 'yes' or 'no' type measurements.

As used herein, "sweat volume" is the fluidic volume in a space that can be defined multiple ways. Sweat volume may be the volume that exists between a sensor and the point of generation of sweat or a solute moving into or out of sweat from the body or from other sources. Sweat volume can include the volume that can be occupied by sweat between: the sampling site on the skin and a sensor on the skin where the sensor has no intervening layers, materials, or components between it and the skin; or the sampling site on the skin and a sensor on the skin where there are one or more layers, materials, or components between the sensor and the sampling site on the skin.

As used herein, "solute generation rate" is simply the rate at which solutes move from the body or other sources into sweat. "Solute sampling rate" includes the rate at which these solutes reach one or more sensors.

As used herein, "microfluidic components" are channels in polymer, textiles, paper, or other components known in the art of microfluidics for guiding movement of a fluid or at least partial containment of a fluid.

As used herein, "state void of sweat" is where a space or material or surface that can be wetted, filled, or partially filled by sweat is in a state where it is entirely or substantially (e.g. >50%) dry or void of sweat.

As used herein, "advective transport" is a transport mechanism of a substance or conserved property by a fluid due to the fluid's bulk motion.

As used herein, "diffusion" is the net movement of a substance from a region of high concentration to a region of low concentration. This is also referred to as the movement of a substance down a concentration gradient.

As used herein, "convection" is the concerted, collective movement of groups or aggregates of molecules within fluids and rheids, either through advection or through diffusion or a combination of both.

As used herein, a "volume-reduced pathway" is a sweat volume that has been reduced by addition of a material, device, layer, or other body-foreign substance, which therefore decreases the chronologically assured sweat sampling interval for a given sweat generation rate. This term can also be used interchangeably in some cases with a "reduced sweat pathway", which is a pathway between eccrine sweat glands and sensors that is reduced in terms of volume or in terms of surfaces wetted by sweat along the pathway. Volume reduced pathways or reduced sweat pathways include those created by sealing the surface of skin, because skin can exchange water and solutes with sweat.

As used herein, "volume reducing component" means any component that reduces the sweat volume. In some cases, the volume reducing component is more than just a volume reducing material, because a volume reducing material by itself may not allow proper device function (e.g., the volume reducing material would need to be isolated from a sensor for which the volume reducing material could damage or degrade, and therefore the volume reducing component may comprise the volume reducing material and at least one additional material or layer to isolate volume reducing material from said sensors).

As used herein "pressure-permeated component" is a component that requires pressure to be permeated by sweat. Pressure-permeated components may also include all known one-way valves, which are opened by pressure, including those known by those skilled in the art of microfluidics. Sweat can be occluded using pressure. In one example, antiperspirants use pressure to stop sweat. Therefore, a pressure-permeated component can be designed to allow sweat flow at the low pressures that correlate with low sweat rates.

As used herein, a "horizontally-confining component" is a component that substantially prevents fluid from spreading horizontally along the skin surface.

As used herein, a "curable fluid or gel" is a fluid or gel that either dries or chemically cures into a solid.

DETAILED DESCRIPTION OF THE INVENTION

This specification builds upon on PCT/US2015/032893, filed May 28, 2015, the disclosure of which is incorporated by reference herein in its entirety. The disclosed invention applies at least to any type of sweat sensing device that measures sweat, sweat generation rate, sweat chronological assurance, its solutes, solutes that transfer into sweat from skin, a property of or things on the surface of skin, or properties or things beneath the skin. The disclosed invention applies to sweat sensing devices which can take on forms including patches, bands, straps, portions of clothing, wearables, or any suitable mechanism that reliably brings sweat stimulating, sweat collecting, and/or sweat sensing technology into intimate proximity with sweat as it is generated. Some embodiments of the disclosed invention utilize adhesives to hold the device near the skin, but devices could also be held by other mechanisms that hold the device secure against the skin, such as a strap or embedding in a helmet.

Certain embodiments of the disclosed invention show sensors as simple individual elements. It is understood that many sensors require two or more electrodes, reference electrodes, or additional supporting technology or features that are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a sweat sensor; an impedance sensor; a sweat volume sensor; a sweat generation rate sensor; and a solute generation rate sensor. Certain embodiments of the disclosed invention show sub-components of what would be sweat sensing devices with more sub-components needed for use of the device in various applications, which are obvious (such as a battery), and for purpose of brevity and focus on inventive aspects are not explicitly shown in the diagrams or described in the embodiments of the disclosed invention. As a further example, many embodiments of the disclosed invention could benefit from mechanical or other means known to those skilled in wearable devices, patches, bandages, and other technologies or materials affixed to skin, to keep the devices or sub-components of the skin firmly affixed to skin or with pressure favoring constant contact with skin or conformal contact with even ridges or grooves in skin, and are included within the spirit of the disclosed invention.

Sweat stimulation, or sweat activation, can be achieved by known methods. For example, sweat stimulation can be achieved by simple thermal stimulation, chemical heating pad, infrared light, by orally administering a drug, by intradermal injection of drugs such as methylcholine or pilocarpine, and by dermal introduction of such drugs using iontophoresis. A device for iontophoresis may, for example, provide direct current and use large lead electrodes lined with porous material, where the positive pole is dampened with 2% pilocarpine hydrochloride and the negative one with 0.9% NaCl solution. Sweat can also be controlled or created by asking the subject using the patch to enact or increase activities or conditions that cause them to sweat. These techniques may be referred to as active control of sweat generation rate.

With reference to FIG. 1, a sweat sensing device 100 is placed on or near skin 12. In an alternate embodiment, the sweat sensing device may be fluidically connected to skin or regions near skin through microfluidics or other suitable techniques. The device 100 is in wired communication 152 or wireless communication 154 with a reader device 150. In one embodiment of the disclosed invention, the reader device 150 is a smart phone or portable electronic device. In alternate embodiments, device 100 and reader device 150 can be combined. In further alternate embodiments, communication 152 or 154 is not constant and could be a simple one-time data download from the device 100 once it has completed its measurements of sweat.

Figure 2:
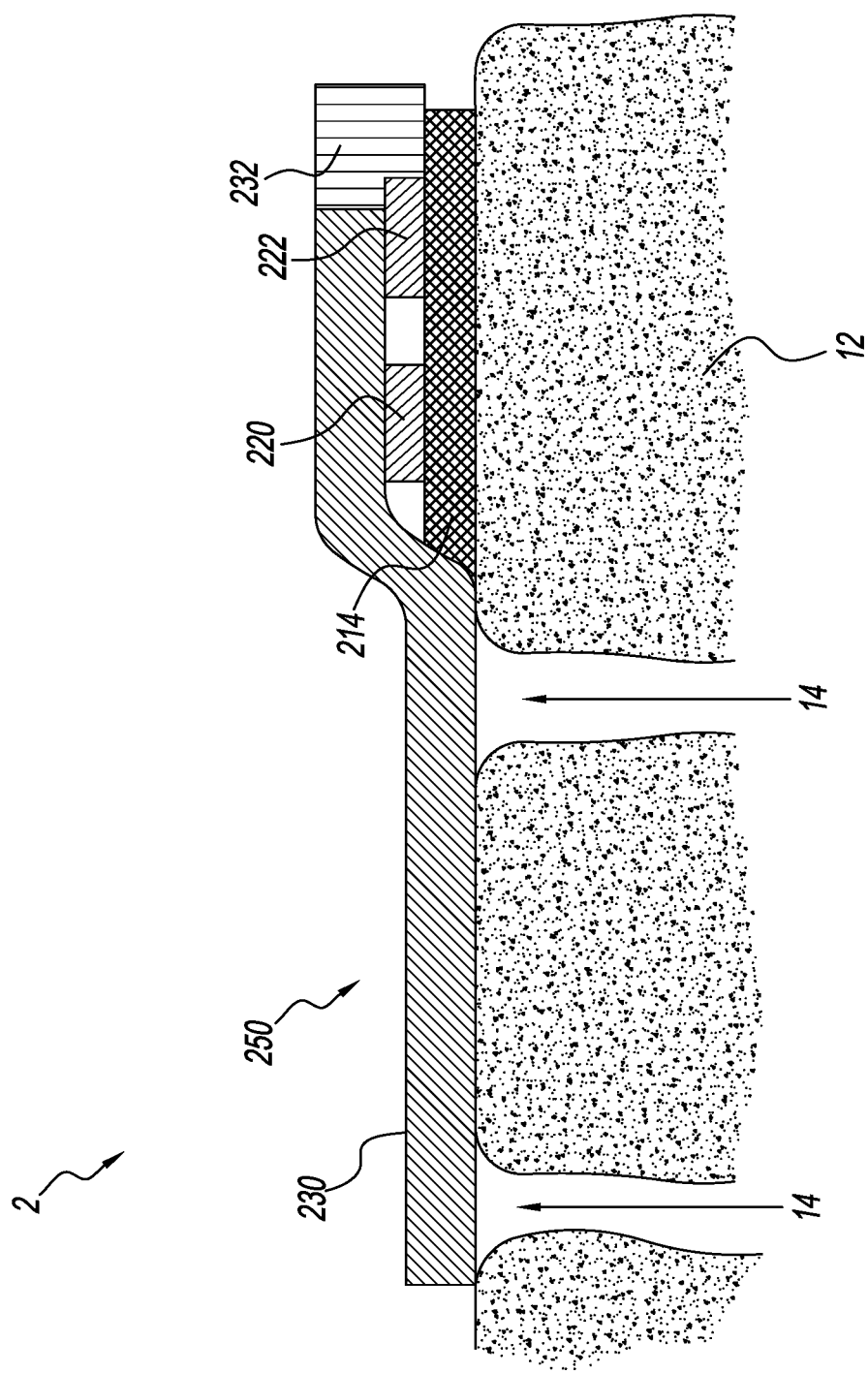
FIG. 2 depicts at least a portion of a wearable device for sweat biosensing.

With reference to FIG. 2, a microfluidic component 230 carries sweat 14 from skin 12 to an analyte-specific primary sensor 220 that is placed on an impermeable substrate 214. The primary sensor 220 measures the presence, concentration, or other property of one or more solutes in sweat. For example, sensor 220 can be an impedance sensor for a cytokine biomarker, an ion-selective electrode to measure sodium, or an electrochemical aptamer-based (EAB) sensor to measure cortisol. One or more secondary sensors 222, such as a drift-free reference electrode, or a sensor to detect the presence of sweat, such as a galvanic skin response sensor, or a sensor to measure the flow rate of sweat, such as a micro-thermal flow rate sensor, or a temperature sensor, or other sensor may also be included. The impermeable substrate 214 can be a polyimide film. The microfluidic component 230 could be, for example, paper, a polymer microchannel, a tube, or a gel, or other means to transport sweat from skin to the sensors. The device is attached to skin by an adhesive (not shown), which can be a pressure sensitive, liquid, tacky hydrogel, which promotes robust electrical, fluidic, and iontophoretic contact with skin. For continuous monitoring, the microfluidic component 230 could wick sweat past the sensors 220, 222 to a hydrogel component 232, that continuously absorbs and pumps sweat from skin 12 and across the sensors at the rate at which sweat is generated from the skin. The device may be covered with a protective component (not shown), made of material such as one that is porous to sweat, one that wicks sweat like a hydrogel or textile, or one that is impermeable to sweat. This example is provided to show that the goals of the disclosed invention may be accomplished in multiple ways, and materials, elements and components of the disclosed invention can function in several configurations. Therefore, the specific example drawings provided should not be interpreted in a limiting manner.

Many sweat sensing device applications place delicate sensors in dynamic environments for extended periods of time, which can expose the sensors to shear, abrasion, compression, or other forces through single or repeated contact with skin, or device components, such as wicking materials. Ionophore sensors and sensors that rely on a monolayer of a probe, such as impedance-based antibody or EAB sensors, are especially vulnerable to damage, which can introduce significant error into measurements of analytes that are present in sweat at very low concentrations (µM to pM and lower). Therefore, some sort of protection for the sensor may be required, and is provided by embodiments of the present disclosure.

Figure 3:
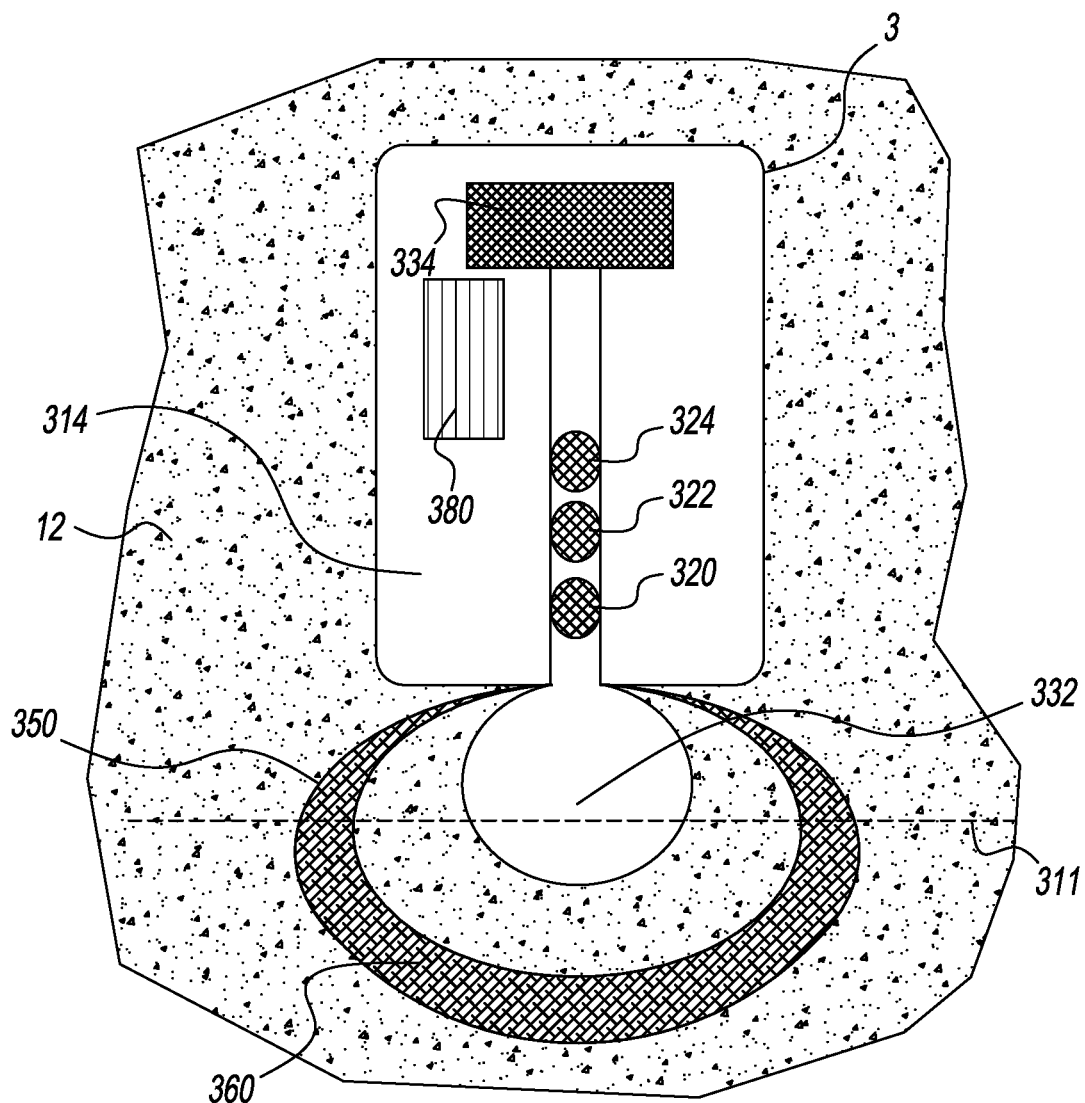
FIG. 3 depicts at least a portion of a wearable device for sweat biosensing.

FIG. 3 presents a top view of at least a portion of the disclosed invention that protects sensors from damage, and in which like numerals refer to like features of previous figures (e.g., 320 is a sensor like sensor 220 of FIG. 2). Embodiments of the disclosed invention may resolve such challenges by having a sensor that can be protected from contact with skin by use of a protective material 332, for example. The device 3 has a sweat impermeable substrate 314 upon which a protective component 332 and electronics 380 are attached. The protective component 332 is in fluidic communication with the sensors 320, 322, 324, and with a pump material 334, and is configured to wick or transport sweat from the skin, across the sensors and to the pump. During use of the device, the skin 12 could move horizontally and abrade against the sensors 320, 322, 324. However, with the inclusion of the protective component 332, the sensors can be placed off the skin, and thereby protected from damage. A variety of materials can be used for the protective component 332, as long as the material is capable of adhesion to device surfaces and skin, and is capable of collecting a sweat sample and transporting the sweat to facilitate sensor function. Non-limiting examples include rayon, a textile, a paper microfluidic material, an aerogel, a low density gel, dialysis membrane material, a porous polymer, nafion, or an in-situ deposited or electro-deposited polymer that is porous and deposited onto the sensor.

Having provided solutions to the problem of sensor abrasion, embodiments of the disclosed invention also have reduced sweat volumes through the use of sensor-centered sweat flow, as disclosed in PCT/US15/32893. Sensor-centered flow involves directing new sweat from sweat glands toward the center of device sensors. To illustrate the advantage of having sensor-centered sweat flow, consider the case where the sweat sample flow is not centered on the sensor. When such a flow of sweat, e.g., one primarily centered to one side or adjacent to the sensor, reaches the sensor, the sensor will see non-uniform sweat flow, with relatively faster flow near where the sweat flow is targeted, and relatively slower flow elsewhere. Having slower sweat flow on part of the sensor will cause older sweat to be measured along with newer sweat, which increases the chronological sampling interval.

For embodiments using circular sensors, having the sweat flow centered on the sensor optimizes sweat sampling rate for a given sweat generation rate, providing sampling rates as much as ~6× faster than a non-centered flow, as taught by Sonner, et al., in *Biomicrofluidics.* 2015 May 15; 9(3): 031301. doi: 10.1063/1.4921039. For embodiments using non-circular sensors, a centered flow would similarly improve sweat sampling rates.

While the theoretical benefits of configuring a sweat sensing device with sensor-centered flow seem apparent, in practice, easily and reliably achieving alignment between device sensors and sweat glands poses a difficulty. Sweat glands are not uniformly distributed in skin, having variations in density between different body parts, and having random distribution in any one area of the body. Therefore, some embodiments of the disclosed invention are configured to allow sensors or other device components to self-align with sweat glands when placed on a device wearer's skin.

Other embodiments are configured to stimulate sweat while minimizing chemical contamination of the resulting sweat sample through use of sudomotor axon reflex (SAR) sweat stimulation, as disclosed in PCT/US2016/17726, which is incorporated herein in its entirety. By using SAR sweat stimulation, the device can stimulate sweat glands within close proximity of a sensor array or sweat sample collector to generate sweat directly underneath the sensors or sweat collector. In combination, SAR sweat stimulation and sensor centered flow can greatly improve sweat sampling rates and reduce necessary sweat volumes, while decreasing contamination of the sweat sample.

With further reference to FIG. 3, the disclosed embodiment protects sensors from damage and implements sensor-centered flow and SAR sweat stimulation. Partially surrounding the protective material 332 is a ring-shaped region 350 containing a sweat stimulation compound 360 such as carbachol, methylcholine, acetylcholine, pilocarpine, or other suitable chemical. The ring shaped region 350 is placed at a distance from the protective material 332, for example between 1 and 5 mm, that optimizes SAR response by sweat glands located directly under the material 332. In some embodiments, the sweat stimulation compound may be introduced to the skin by iontophoresis. Preferentially, however, sweat stimulation will occur by passive diffusion into the skin, which may need to be facilitated by skin surfactants or chemical penetration enhancers as used in the art of transdermal drug delivery, for example by suspension in diols such as propylene glycol. See, Pathan, I., et al., "Chemical Penetration Enhancers for Transdermal Drug Delivery Systems," *Tropical Journal of Pharmaceutical Research*, April 2009; 8 (2): 173-179.

Figure 4:
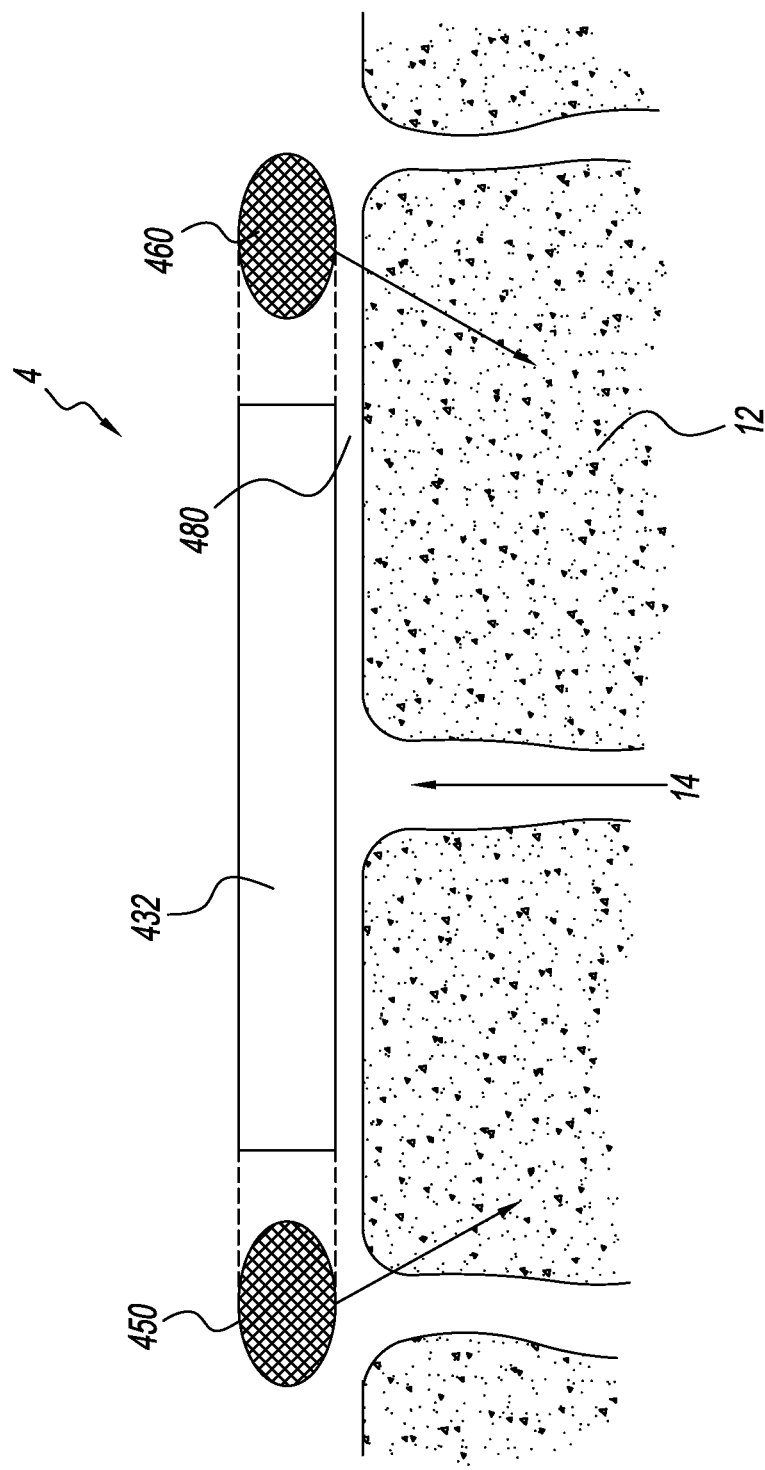
FIG. 4 depicts at least a portion of a wearable device for sweat biosensing.

FIG. 4 is an alternate, cross-sectional view of the embodiment depicted in FIG. 3, as bisected along axis 311, and in which like numerals refer to like features of previous figures. The device 4 includes a protective component 432, and ring-shaped region 450 containing sweat stimulating compound 460. The device is placed on skin 12 over an eccrine sweat duct 14, and having a sweat volume 480 under the protective component 432. Sensor-centered flow can be facilitated by appropriately configuring the protective component 432 to directly and efficiently direct sweat across the sensors using known microfluidic techniques. For example, the skin-facing side of the protective component 432 may include a polymer with defined trenches to facilitate sweat flow, where the bottom of said trenches is the surface of a sweat impermeable membrane. Such trenches could have a geometry that promotes directional capillary flow, and therefore can be designed to move sweat toward the sensors. For example, if sweat wetted such a trench mid-way between the edge of the protective component and its radial center, then the sweat would wick to the radial center of the protective component 432, and from there to the sensors.

Figure 5:
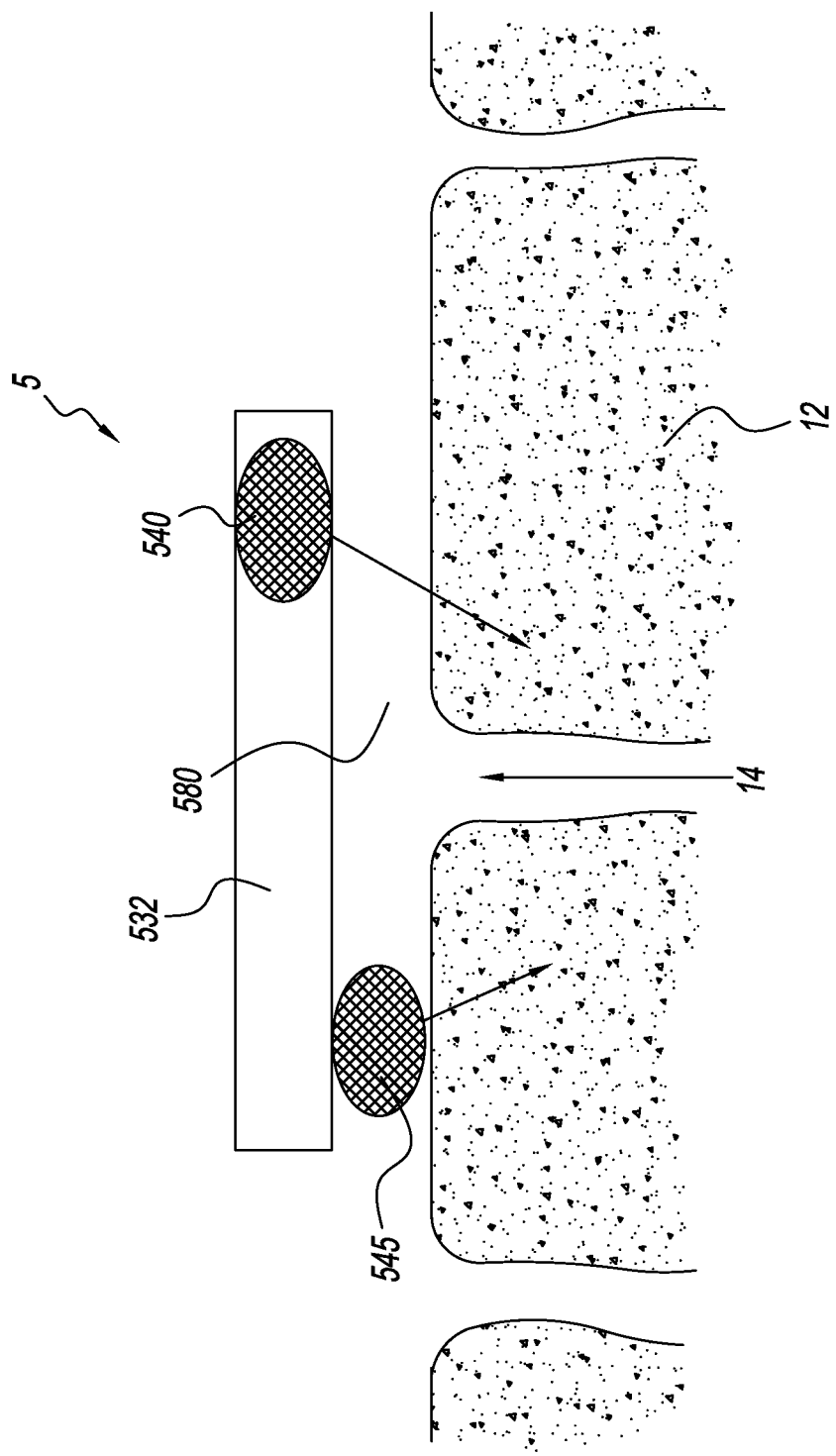
FIG. 5 is a cross-sectional view of at least a portion of a wearable device for sweat biosensing with sensors and sweat stimulation means that self-align with sweat ducts.

With reference to FIG. 5, where like numerals refer to like features of previous figures, in some embodiments, the device 5 may not include a ring shaped region, but instead would include a sweat stimulating compound inside 540, or on 545, the protective component 532. Other embodiments (not shown) may include both a ring-shaped region, and stimulating compound incorporated in the protective component. Co-locating the stimulating compound with the protective component as depicted may increase the likelihood of contamination of sweat samples by the stimulating compound. Therefore, the stimulating compound locations may need to be patterned on, or in, the protective component 532 to reduce contamination, or the component may include microfluidic channels, barriers, or track-etched membranes (not shown) to prevent or reduce contamination. As in the previous example, the protective component 532 may include a polymer on its skin-facing surface having defined trenches to facilitate sweat flow. However, in this embodiment, the trenches move uncontaminated sweat toward the sensors and move chemically-contaminated sweat away from the sensors. In this embodiment, for example, if sweat wetted a trench mid-way between the edge of the protective component and its radial center, then the sweat would still wick to the radial, but if sweat wetted the trench closer to the edge, the trench would wick the sweat away from the radial center, and out of the device.

Figure 6:
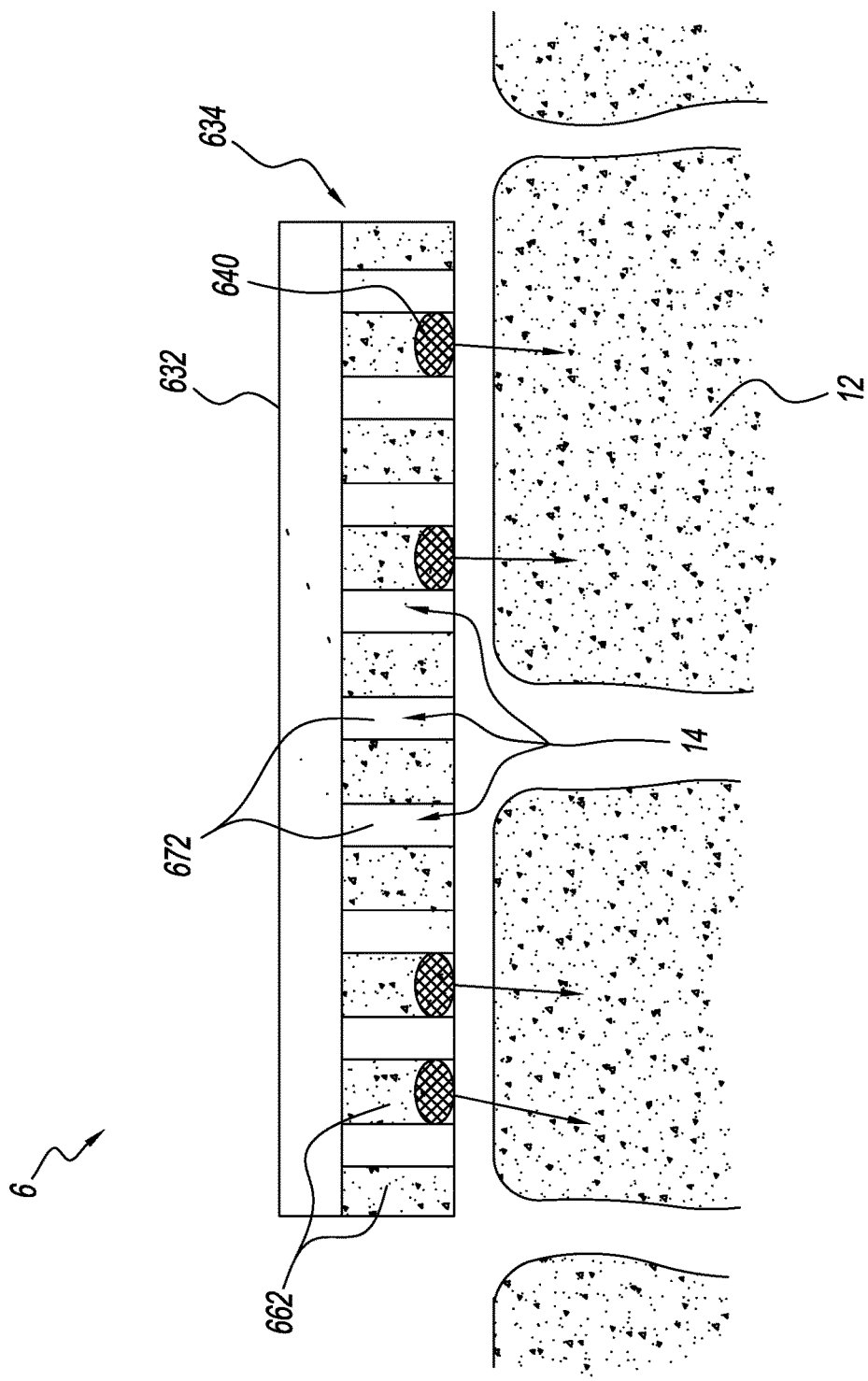
FIG. 6 is a cross-sectional view of at least a portion of a wearable device for sweat biosensing with sensors and sweat stimulation means that self-align with sweat ducts.

With reference to FIG. 6, where like numerals refer to like features of previous figures, a device 6 further includes a wicking material 634 that is configured to reduce sweat volume. Wicking material 634 has blocking areas 662 that largely prevent the flow of sweat, and flow areas 672 that allow sweat flow. In a preferred embodiment, the blocking areas would be >90% of the available surface area of material 634, which would reduce effective sweat volume by >100×. The wicking material 634 could be a layer of very thin paper or printed nano-cellulose, impregnated with wax to create blocking areas, as known by those skilled in the art of paper microfluidics. In all embodiments, cellulose or nano-cellulose could be replaced with polymer or other microfibers that may have less non-specific analyte absorption or some other desirable property. Additionally, when the device is placed on the skin, some flow areas will be aligned over sweat ducts 14, while others are not. The flow areas placed over a sweat duct would form a volume-reduced pathway for sweat. Likewise, flow areas not over a sweat duct and blocking areas would not be a part of the volume-reduced pathway. Therefore, the device will also self-align with sweat ducts to provide a sweat flow that is centered on the sensor.

Within a plurality of blocking areas 662 of the wicking material 634, some embodiments can be configured with a sweat stimulating compound 640, such as carbachol, acetylcholine, or methylcholine. The compound 640 may be arranged in different patterns to optimize sweat stimulation and minimize contamination of the sweat sample for various applications. Within the blocking areas, the compound would be separated from the skin by a sweat-dissolvable barrier, such as a material that dissolves in the presence of low pH solutions. In some embodiments, the compound may be co-formulated or mixed with an agent facilitating time release of the compound. Such time-release agents and techniques could be, for example, slow-release binders such as biocompatible polymers and copolymers, carrier agents that slow release, or agents that delay absorption of the stimulating compound, all as known in the art of sustained release chemistry. When activated, the sweat stimulating compound would diffuse into skin 12 slowly over time, for example over a 24-hour period. As with other embodiments, glycol, iontophoresis, or other means may be required to facilitate sweat stimulation. In this manner, the disclosed invention can supply low levels of prolonged sweat stimulation to facilitate continuous measurement of sweat analytes with minimal irritation to the device wearer, and with controlled sweat generation rates.

Figure 7:
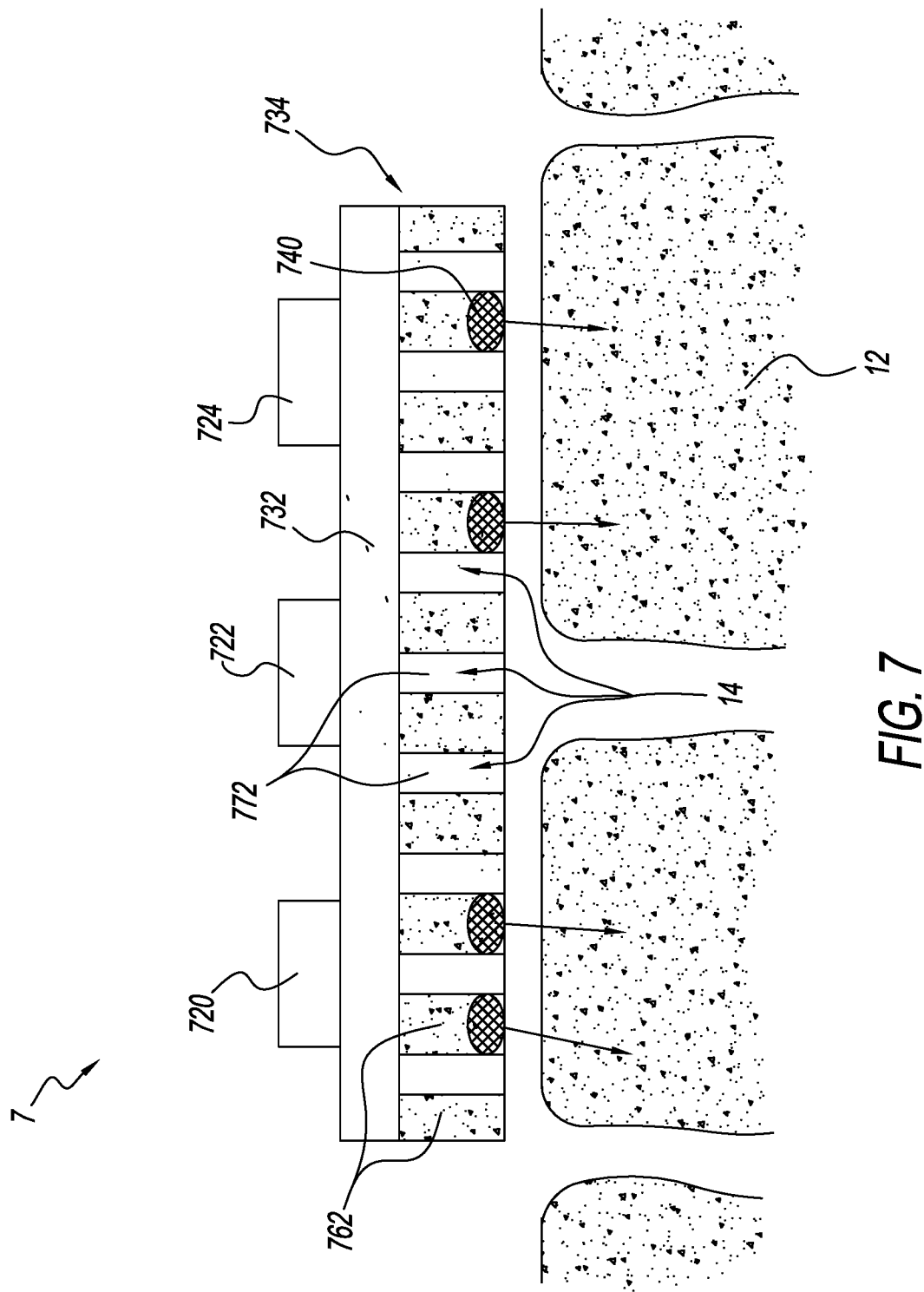
FIG. 7 is a cross-sectional view of at least a portion of a wearable device for sweat biosensing with sensors and sweat stimulation means that self-align with sweat ducts.
Figure 7A:
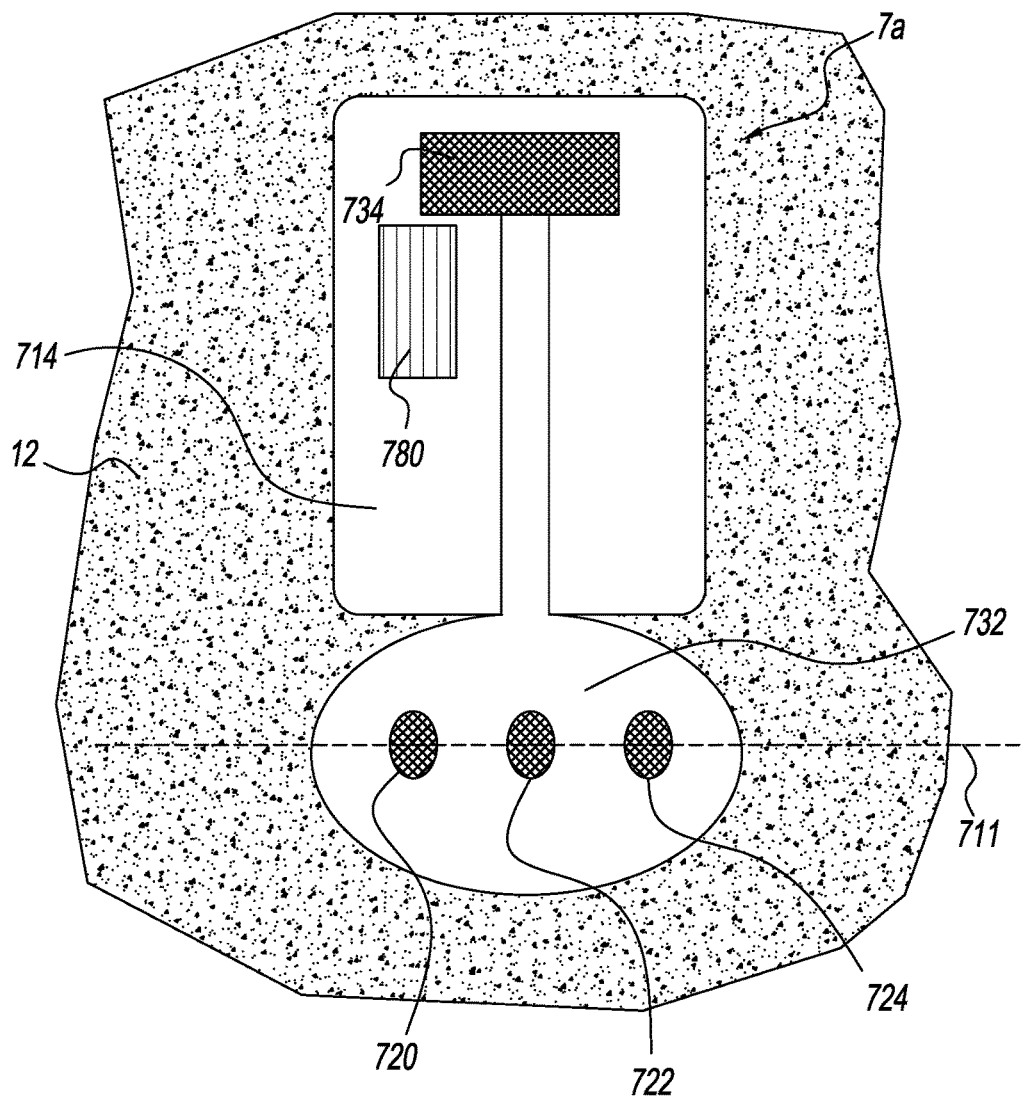
FIG. 7A is a top view of at least a portion of a wearable device for sweat biosensing with sensors and sweat stimulation means that self-align with sweat ducts.

With reference to FIG. 7, in another embodiment of the disclosed invention, the device 7 includes sensors 720, 722, 724, configured on the protective material 732. This configuration protects the sensors from damage due to skin contact, and allows for a lower chronologically-assured sweat sampling interval by reducing overall sweat volume. FIG. 7A is a top view of the same embodiment with the depicted axis 711 illustrating the location of the cross-sectional view in FIG. 7.

This has been a description of the disclosed invention along with a preferred method of practicing the disclosed invention, however the invention itself should only be defined by the appended claims.

What is claimed is:

1. A wearable sweat sensing device, comprising:
   a sensor configured to measure a characteristic of an analyte in a sweat sample, and when the device is placed on a device wearer's skin, the sensor is configured to be located at a first distance from an aligned sweat gland located in the device wearer's skin, and at a second distance from an unaligned sweat gland located in the device wearer's skin, wherein the first distance is less than the second distance;
   an abrasion protector supporting the sensor, wherein the abrasion protector is configured to reduce a volume of sweat required to fill between the wearer's skin and the sensor, wherein the abrasion protector is configured to be located between the sensor and the device wearer's skin, wherein the abrasion protector includes one or more channels fluidically connecting the sensor with the aligned sweat gland, and wherein the one or more channels have lengths between the first distance and the second distance; and
   a wicking material configured to be located between the abrasion protector and the device wearer's skin, wherein the wicking material is configured to reduce a volume of sweat required to fill between the wearer's skin and the sensor; wherein the wicking material includes a plurality of blocking areas configured to resist a flow of sweat, and a plurality of flow areas configured to allow a flow of sweat, and wherein one or more of the plurality of flow areas fluidically connect the sensor with the aligned sweat gland.

2. The device of claim 1, further comprising a compound for stimulating sweat generation, wherein the stimulating compound is configured to be delivered to the wearer's skin.

3. The device of claim 2, wherein the stimulating compound stimulates sudomotor axon reflex sweating.

4. The device of claim 2, further comprising an iontophoresis electrode configured to deliver the compound to the wearer's skin.

5. The device of claim 2, further comprising a substance to improve absorption of the sweat stimulating compound into the wearer's skin, wherein the substance is one of the following: a skin surfactant; or a penetration enhancer.

6. The device of claim 2, wherein the stimulating compound is one of the following: carbachol; methylcholine; acetylcholine; or pilocarpine.

7. The device of claim 2, wherein the abrasion protector and wicking material are configured to minimize contamination of the sweat sample by the stimulating compound.

8. The device of claim 2, wherein the abrasion protector includes one of the following: a microfluidic channel, a barrier, or a track-etched membrane.

9. The device of claim 2, wherein the stimulating compound is configured to cause the aligned sweat gland to generate sweat.

10. The device of claim 2, wherein the stimulating compound is configured in a semicircular pattern around the abrasion protector.

11. The device of claim 2, wherein the stimulating compound is in one of the following locations: on the abrasion protector; within the abrasion protector; within the wicking material.

12. The device of claim 2, wherein the stimulating compound is configured to facilitate sustained release into the device wearer's skin to cause controlled and prolonged sweat generation.

13. The device of claim 12, wherein the stimulating compound further comprises one of a biocompatible time-release agent; or a barrier compound.

14. The device of claim 2, wherein the sweat stimulating compound is located in the plurality of blocking areas.

15. The device of claim 1, wherein the abrasion protector and wicking material are configured so that the one or more channels cause a flow of sweat to be directed to a center of the sensor.

16. The device of claim 1, wherein the wicking material comprises a surface area having greater than ninety percent (>90%) blocking areas and less than 100% blocking areas.

* * * * *